Figure 5:
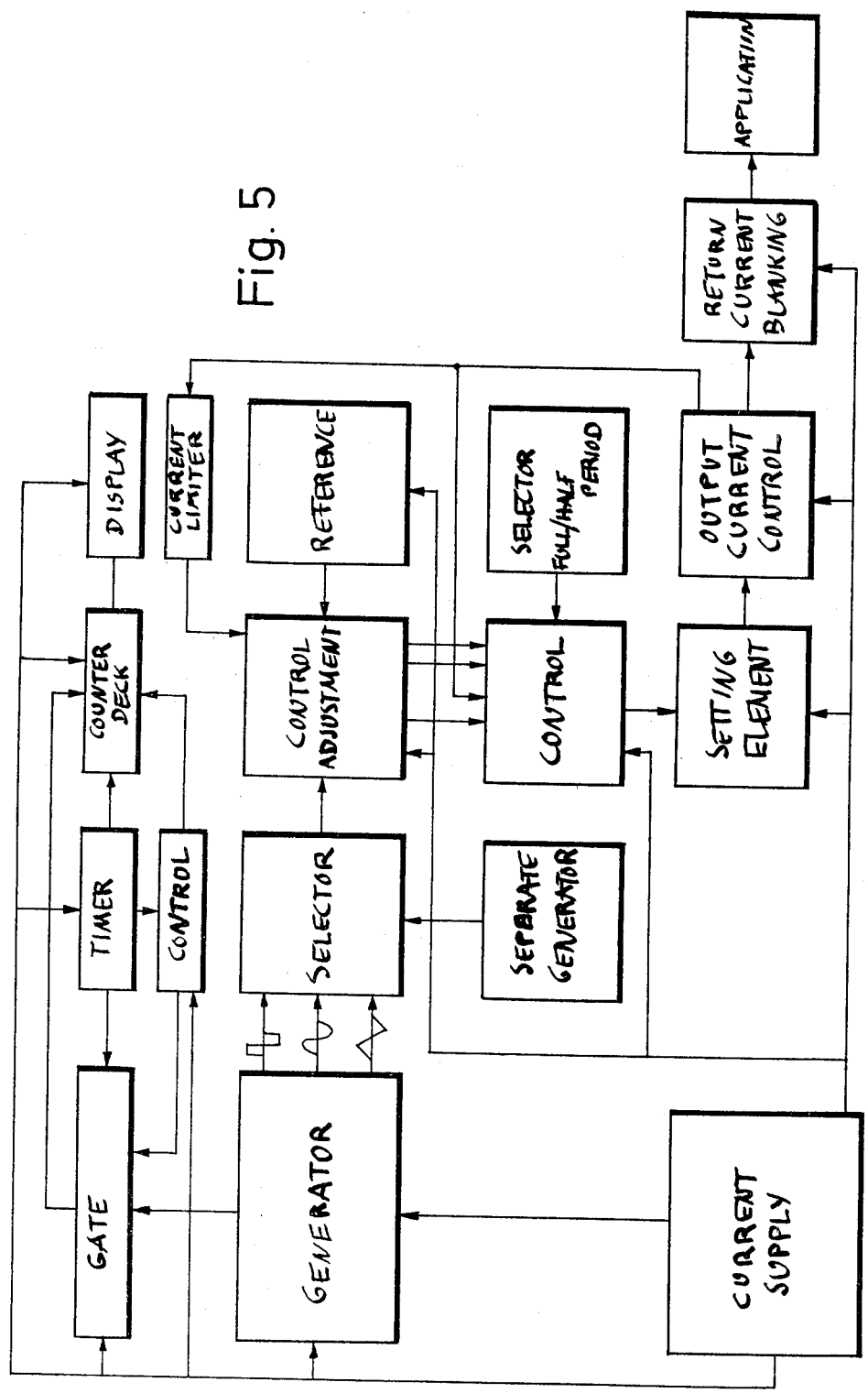

United States Patent [19]

Kief

[11] 4,262,672
[45] Apr. 21, 1981

[54] ACUPUNCTURE INSTRUMENT

[76] Inventor: Horst Kief, Londoner Ring 105-107, D-6700 Ludwigshafen/R, Fed. Rep. of Germany

[21] Appl. No.: 974,094

[22] Filed: Dec. 28, 1978

[30] Foreign Application Priority Data

Jan. 2, 1978 [DE] Fed. Rep. of Germany ....... 2800039

[51] Int. Cl.³ ............................................. A61B 17/34
[52] U.S. Cl. ................................. 128/329 A; 128/422
[58] Field of Search ........... 128/419 P, 419 R, 329 A, 128/734–735, 303.18

[56] References Cited

U.S. PATENT DOCUMENTS

| 3,207,151 | 9/1965 | Takagi | 128/419 R |
| 3,357,434 | 12/1967 | Abell | 128/419 P |
| 3,900,020 | 8/1975 | Lock | 128/303.18 X |
| 3,908,669 | 9/1975 | Mon et al. | 128/329 A |
| 3,946,745 | 3/1976 | Loi et al. | 128/329 A |
| 3,957,053 | 5/1976 | Woo | 128/329 A |
| 4,098,277 | 7/1978 | Mandell | 128/329 A |

Primary Examiner—Robert W. Michell
Assistant Examiner—Francis J. Jaworski
Attorney, Agent, or Firm—Kurt Kelman

[57] ABSTRACT

An acupuncture instrument for use in producing analgesia comprises a needle having a head and an electrical connection for applying a transformer arrangement including an electric coil constituting a secondary winding of the transformer arrangement and having two poles, one of the poles being insulated therefrom, the electric coil being arranged on the needle head and being capable of being surrounded by another coil constituting a primary winding of the transformer arrangement, and an annular electrode electrically connected to the other pole of the secondary winding and insulated with respect thereto and vertically movably arranged on the secondary winding.

12 Claims, 5 Drawing Figures

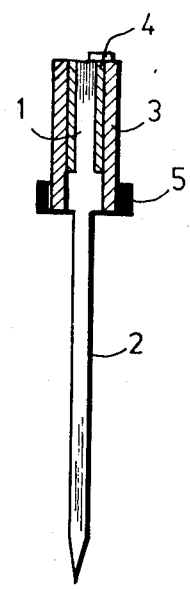
Fig.1
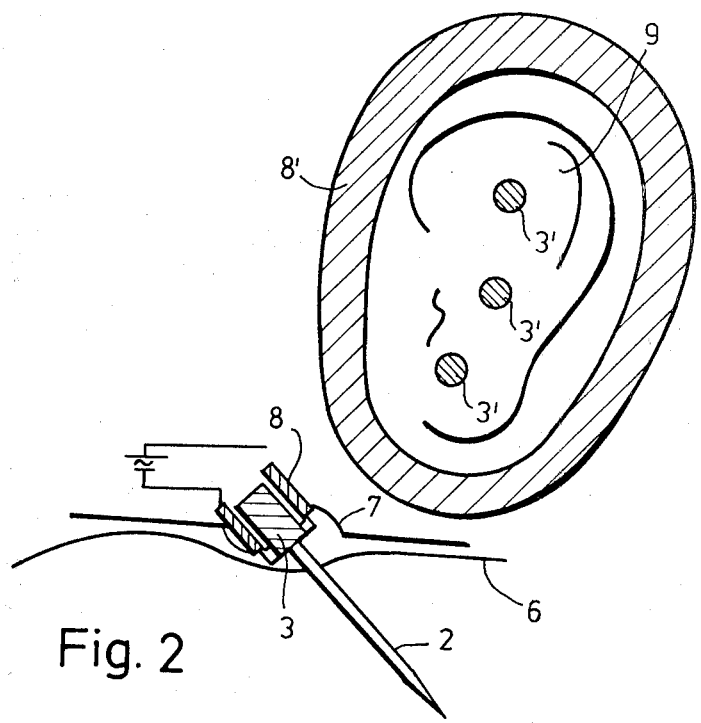
Fig. 3
Fig. 2
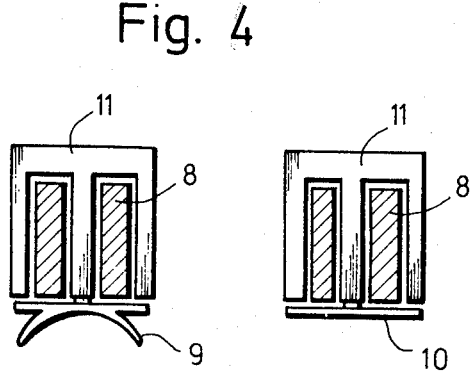
Fig. 4

ACUPUNCTURE INSTRUMENT

The invention relates to an acupuncture instrument with a needle which is provided with a connection for electrical pulses.

The effective use of acupuncture needles for producing analgesia has been proven. The production of endorphines, which are substances formed in the body and which are 200 times stronger than morphine, has been experimentally triggered by acupuncture and difficult operations in various parts of the body have been performed under acupuncture analgesia. In all of this acupuncture analgesia, electric current is utilized as stimulating agent to an increasing extent. For this purpose, current pulses in the range of milliamperes up to a voltage of 40 Volts and of sinuous, rectangular or triangular and mixed shapes, are transmitted by the needle to the body at certain points to be selected. This has been done up to now in the simplest manner by connecting the needle by very small crocodile clips to the pulse generator. The needles for the acupuncture analgesia are so formed that they simultaneously serve as coupling for a plug connection. Although this has the advantage of a relatively secure connection while leaving the electrical conductor easily detachable, it has the considerable disadvantage of direct manipulation on the needle when the coupling is emplaced and thus, particularly in the case of short needles, the danger of removing the point of the needle from the center of the acupuncture spot. During operations of longer duration, this danger may also arise spontaneously, of course, and requires increased attention by the anesthetist.

The invention has the object of providing an acupuncture instrument with which optimal conditions of anesthesia as well as of therapeutic treatment may be attained while the needle used for this purpose is not displaced from its accurate position by the electrical connection.

This object has been accomplished according to the invention by arranging an electrical coil on the head of the needle, on which a second coil may be mounted, the latter coil constituting the primary winding and the other coil constituting the secondary winding of a transformer arrangement.

This type of inductive pulse transmission has the decisive advantages of making possible easy sterilization of the needle with the secondary winding, the avoidance of manipulation of the needle when it is connected to the pulse instrument and the absolute fixation of the needle on a selected acupuncture spot by means of the primary winding.

The needle with an "induction winding head" has the further advantage that several needles, which may be placed at different spots, may be stimulated with suitable pulses in rapid succession to increase their effectiveness without an electrically conductive connection with a primary winding which may be easily moved and manipulated. More recent forms of acupuncture treatment have proved that the forms of the pulses are therapeutically less decisive than the direction of the current of the individual pulse shapes. This result has not been taken into account in conventional generators. It appears to be sensible, therefore, to block the undesired current direction of the respective pulses by diodes in the therapeutic use of electric current in acupuncture therapy. In this manner, a desired sedative or stimulating effect according to the Yin-Yan-principle is obtained. On the other hand, experience has shown that, in contrast to the desired therapeutic effect of monophase pulses, biphase pulses are apparently more effective in acupuncture for analgesia, a pulse shape which is rectangular in the positive portion and exponential in the negative portion apparently being particularly effective.

Since a large portion of the points important for acupuncture analgesia are near the ear, it is sensible to adapt the primary winding specifically for this purpose to the anatomical shape of the ear, similar to an earphone, and thereby to obtain an ideal fixation of the primary winding. Essentially, this is an anatomically formed open coil ring with earphone harness so that the needle may be changed during therapy, too. Particularly at the ear, where several needles are frequently actuated simultaneously with one primary winding, it is advantageous to use needles with interchangeable secondary windings since some spots must be treated to stimulate or sedate in the sense described hereinabove, and it has been found that this result may be obtained most readily by exchanging windings wound to the right by windings wound to the left, that is exchanging coils south-to-north pole. Exact controls of the acupuncture effect on the human body by the measurement of the capacity of the so-called meridians have shown that an acupuncture point may be influenced directly, that is without needle, with surprising effectiveness by suitably increasing the field strength of the primary winding of the application instrument, this effect being dependent on the frequency, the field strength and, most of all, dependent on whether the north or the south pole of the winding faces the acupuncture point. Therefore, it is advantageous to control the magnetic field strength stepwise, the weaker step being applied when needles are used and the considerably stronger step being applied in therapy forms without needles.

The examination of therapeutic success in dependence on the frequency showed that a particularly harmonizing effect on the organism is obtained when not only very low frequency pulses of about 5–25 Hz are transmitted to the acupuncture point but if this is done in the form of bundles of pulses, the frequencies of the individual pulses being proportional by an integer to the prevailing basic frequency, as is known also from the high tone series in musical harmony. The overlapping frequencies, therefore, are in the relation of thirds, fourths, fifths, octaves etc. This means that pulses with overlapping frequencies of 8, 16, 32, 64, 128, 256, 512 1024 etc. ($2^{n+3}$) per second are simultaneously transmitted in one point to the acupuncture point. The above-mentioned novel meridian diagnosis shows that certain points are in an antagonistic relationship, i.e. when therapeutic effects are obtained above a certain point by stimulating pulses, they could also be obtained by sedative pulses by its antagonistic counter player. Therefore, the effect was correspondingly powerful when both points were used while simultaneously applying opposite pulses. Such a pulse generator must accordingly be capable of delivering simultaneously pulses of opposite phases. This type of application is also available, for example in acupuncture analgesia, to obtain especially intensive current surges in the region to be subjected to analgesia with the pulse transmission described hereinabove. However, when the acupuncture needle with induction winding is used for therapeutic purposes, the unidirectional conductive connection secondary winding-needle is fully sufficient to obtain a therapeutic effect by the minimal current flowing towards ground potential. This current may be amplified by placing the patient on an electrode sheet of metal, for instance negatively charged and connected to ground potential, with a positive needle pulse. On the other hand, a selective point effect is obtained when the one end of the winding is connected to the needle while the other is connected to the annular electrode which is mounted about the winding. A mode of application exclusively with primary windings constitutes another possibility of application, particularly for example with children sensitive to pain, the above-described variation possibilities being, of course, available. In this case, it is particularly advantageous to surround the winding with a ferrite sleeve to obtain as high a directed field density at the acupuncture point as possible. An especially differentiated and also protracted therapy may be obtained with windings whose application sides have bonding or suction faces which are placed on acupuncture points to be selected, direction and strength of the magnetic field being determined in dependence on the desired effect. This method may be applied with primary as well as secondary windings which receive their energy in common from an applied large field. It has been known for a long time that acupuncture points can be therapeutically treated not only by insertion of a needle but also by application of heat, known as maxibustion. This multi-faceted form of therapy may be very easily executed by replacing the point of the ferrite rod positioned in the primary winding by a soft iron point which is heated more rapidly due to its other magnetic properties and thereby makes possible a simultaneous heat application to the acupuncture point.

The invention is explained further in the description hereinbelow in conjunction with exemplary embodiments.

Shown is in

FIG. 1 a first embodiment of an acupuncture instrument according to the invention, with the utilized needle, FIG. 2 another embodiment of the instrument, FIG. 3 still another embodiment;

FIG. 4 two modifications of applying the primary winding and

FIG. 5 a block circuit diagram of the pulse generator with control arrangement.

In the embodiment according to FIG. 1, a ferrite core 4 is arranged on head 1 of a needle 2, a secondary winding 3 being replaceably mounted thereon. One pole of the winding is electrically connected to the needle. The other pole may be connected to an insulated annular electrode 5 which is vertically displaceably arranged about secondary winding 3. The primary winding is not illustrated in this embodiment but it may be mounted over this arrangement.

Needle 2 is shown positioned in web 6 in the further embodiment according to FIG. 2, second winding 3 being fixedly connected to the head of the needle while primary winding 8 is loosely placed over secondary winding 3. The primary winding is carried by a movable holder 7.

Finally, FIG. 3 shows a primary winding 8' in the shape of a headphone which may be placed over ear 9, several secondary windings 3' being arranged on the corresponding acupuncture points which lie within primary winding 8'.

Fundamentally, three embodiments are possible for the arrangement of the primary winding, that is:

(1) as radiation rod, wherein the primary winding is placed on the web at a suitable position,
(2) as movably positioned primary winding 8 according to FIG. 2,
(3) as a primary winding anatomically suited to the ear, similar to a stereo headphone, as illustrated in FIG. 3, or
(4) as a primary winding with a suction or bonding face.

FIG. 4 shows two modifications for the arrangement of primary winding 8, the primary winding being provided with an iron core 11 and being applicable to the acupuncture point for long-term therapy in the one case by means of suction cup 9 and in the other case by bonding face 10.

In the block circuit diagram according to FIG. 5, the individual blocks have been designated suitably so that it is sufficient to explain the operation. The generator delivers various shapes of curves of which each may be individually shaped again, for example in the lower portion by an exponential component. The selector selects the curve shape selected by the therapist for application. These signals are transmitted to a control amplifier. The control amplifier transmits the signals to the control. The control may be considered as a power control wherefore the control amplifier is connected to the input. Voltage control, current limitation and pulses from the selector, that is full or half periods of the pulses or the displacement of the pulses in the positive or negative half-phase, are transmitted to the control. The setting element is fundamentally provided in the range of the control already. It is required to reach higher capacities in case of a direct magnetic field application, for example. The control of the output current is required to monitor the output voltage and the output current intensity. It furthermore comprises a gauge for the winding current. Current blanking is required to reduce the self-induction to protect the patient. The current blanking is switched off in the case of a biphase pulse because the self-induction is automatically canceled in this case.

What is claimed is:

1. An acupuncture instrument comprising a needle having a head and an electrical connection for applying electrical pulses to the needle, the electrical connection being a transformer arrangement including an electrical coil constituting a secondary winding of the transformer arrangement and having two poles, one of the poles being electrically connected to the needle and the other pole being insulated therefrom, the electric coil being arranged on the needle head and being capable of being surrounded by another coil constituting a primary winding of the transformer arrangement, and an annular electrode electrically connected to the other pole of the secondary winding and insulated with respect thereto and vertically movably arranged on the secondary winding.

2. The acupuncture instrument of claim 1, further comprising a ferrite core mounted on the needle head, the electric coil constituting the secondary winding being arranged on the core.

3. The acupuncture instrument of claim 1 or 2, wherein the electric coil constituting the secondary winding is replaceably mounted on the needle head.

4. The acupuncture instrument of claim 1 or 2, further comprising the other coil constituting the primary winding, the other coil having the shape of an annular headphone and surrounding the electrical coil constituting the secondary winding.

5. The acupuncture instrument of claim 1 or 2, further comprising the other coil constituting the primary winding, the other coil carrying a detachable soft iron point.

6. The acupuncture instrument of claim 1 or 2, further comprising a pulse generator including a control circuit connected to the electrical connection for transmitting electrical pulses of selected shapes to the needle.

7. The acupuncture instrument of claim 6, wherein the control circuit is capable of interchanging the poles.

8. The acupuncture instrument of claim 6, wherein the control circuit is capable of selecting a desired half phase of the electrical pulses for transmission.

9. The acupuncture instrument of claim 8, comprising two of said needles and the control circuit is connected to the electrical connections of both needles for simultaneously transmitting thereto respective ones of the half phases.

10. The acupuncture instrument of claim 1 or 2, further comprising the other coil constituting the primary winding and means for holding the coils on the needle.

11. The acupuncture instrument of claim 10, wherein the holding means is a suction means.

12. The acupuncture instrument of claim 10, wherein the holding means is a bonding means.

* * * * *